United States Patent [19]
Le et al.

[11] Patent Number: 5,894,921
[45] Date of Patent: *Apr. 20, 1999

[54] PACKAGE FOR SUTURE ANCHOR

[75] Inventors: Thu Anh Le, Matawan, N.J.; Robert J. Cerwin, Pipersville, Pa.

[73] Assignee: Ethicon, Inc., New Brunswick, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/946,468

[22] Filed: Oct. 7, 1997

[51] Int. Cl.$^6$ .................................... A61B 17/06
[52] U.S. Cl. ........................................ 206/63.3
[58] Field of Search .................. 206/63.3, 227, 206/380, 382, 303

[56] References Cited

U.S. PATENT DOCUMENTS

| 4,946,468 | 8/1990 | Li . | |
|---|---|---|---|
| 5,002,550 | 3/1991 | Li . | |
| 5,249,671 | 10/1993 | Sinn . | |
| 5,271,495 | 12/1993 | Alpern | 206/63.3 |
| 5,540,718 | 7/1996 | Bartlett . | |
| 5,575,382 | 11/1996 | Sobel et al. | 206/63.3 |
| 5,626,612 | 5/1997 | Bartlett . | |
| 5,715,942 | 2/1998 | Li et al. . | |
| 5,733,293 | 3/1998 | Scirica et al. | 606/144 |

*Primary Examiner*—Paul T. Sewell
*Assistant Examiner*—Nhan T. Lam
*Attorney, Agent, or Firm*—Emil Richard Skula

[57] ABSTRACT

A package for a suture anchor and attached suture. The package has on a top side a suture channel covered by door members. The bottom side of the package has a suture anchor mounting chamber and channel as well as a needle park for surgical needles.

6 Claims, 12 Drawing Sheets

PACKAGE FOR SUTURE ANCHOR

TECHNICAL FIELD

The field of art to which this invention pertains is packaging for medical devices, more specifically, packages for suture anchors.

BACKGROUND OF THE INVENTION

Suture anchors are medical devices which are used to attach soft tissue to bone. A suture anchor can have a variety of configurations. One type of suture anchor, such as that disclosed in U.S. Pat. No. 4,898,156, which is incorporated by reference, has superelastic arc members extending from an anchor member. Other suture anchors have screw threads and cutting flutes such as those disclosed in U.S. Pat. No. 4,632,100, which is incorporated by reference. Yet another suture anchor configuration can be described as a wedge type anchor as disclosed in commonly owned copending U.S. patent application Ser. No. 08/235,737 (Docket No. ETH-923), which is incorporated by reference.

Suture anchors typically have mounting members, such as eyelets, for receiving a surgical suture. Typically, a surgical needle is mounted to each end of the suture. The initial step in a surgical procedure using a suture anchor to mount soft tissue to bone is for the surgeon to drill a blind bore hole in bone using a conventional surgical drill. Then, a suture anchor, typically mounted to the distal end of an application device, is inserted into the bore hole such that the anchor body is lodged in the bone beneath the hard outer cortex of the bone, such that the surgical suture extends out from the bone bore hole. Next, the surgeon, utilizing the surgical needles attached to the surgical suture, affixes soft tissue adjacent to the bone surface. The surgeon then secures the approximated soft tissue with the suture using conventional surgical knots and knotting techniques, and finally cuts the surgical needles and excess suture away from the knots. The soft tissue is now approximated next to an appropriate bone site where it can heal and reattach to the bone surface. The types of soft tissue which can be approximated include ligaments, tendons, cartilage, muscle, skin, organs and the like.

It is critical that the suture anchor and surgical suture and attached needles be easily removed from a package during surgery. It is also critical that the package protect the suture anchor, suture and needles during sterilization, and store and handling prior to use in a surgical procedure.

There is a need in this art for novel packages for suture anchors which provide superior ease of use in the field during surgical procedures, and which are economical to manufacture while still protecting the suture anchor, sutures and needles during shipping, handling and storage.

SUMMARY OF THE INVENTION

It is an object of the present invention to provide a novel package for a suture anchor which is economical to manufacture and which provides good protection to a suture anchor and attached surgical suture and needles during sterilization, storage, shipping and handling.

It is a further object of the present invention to provide a suture anchor package which allows for smooth release of sutures and needles from the package without hang-ups.

It is still yet a further object of the present invention to provide a suture anchor package which allows an anchor to be easily mounted to an applicator and withdrawn from the package.

Accordingly, a novel package for a suture anchor is disclosed. The package has a base member having a top, a bottom and an outer periphery. An outer wall extends upwardly from the top of the base member about the outer periphery. An inner wall extends upwardly from the top of the base member, said wall is positioned inwardly from the outer wall, and is separated from the outer wall by a section of the top of the base member such that the inner wall, the outer wall and the section of the top of the base member form a suture winding channel. A cover member is mounted to the top of the base member. The cover member comprises a bottom member having a central opening, and an outer periphery. An outer wall extends up from the outer periphery, said outer wall having a top. A plurality of cantilevered door members each having a fixed end and a free end extend radially out from the top of the inner wall, wherein said door members are spaced apart by having spaces or gaps in between. There is an opening extending through the base member for receiving at least one strand of suture. A foam member is mounted on the bottom of the base member for parking needles. First and second spaced apart parallel walls extending from the bottom of base member form a suture anchor mounting channel, each of said first and second walls has an inner side and an outer side. A plurality of shaft engagement walls extend perpendicularly from the inner sides of the first and second parallel walls, said walls extend partially into the suture anchor mounting channel. Means extend from the bottom of the cover member for mounting to the base member such as, for example, locking pins. And, there are means in the base member for receiving the mounting means of the cover member, such as retaining holes. The cover member is mounted to the base member such that the cantilevered members extend over the suture channel.

Other features and advantages of the invention will become more apparent from the following description and accompanying drawings.

DESCRIPTION OF THE PREFERRED EMBODIMENTS

Figure 1:
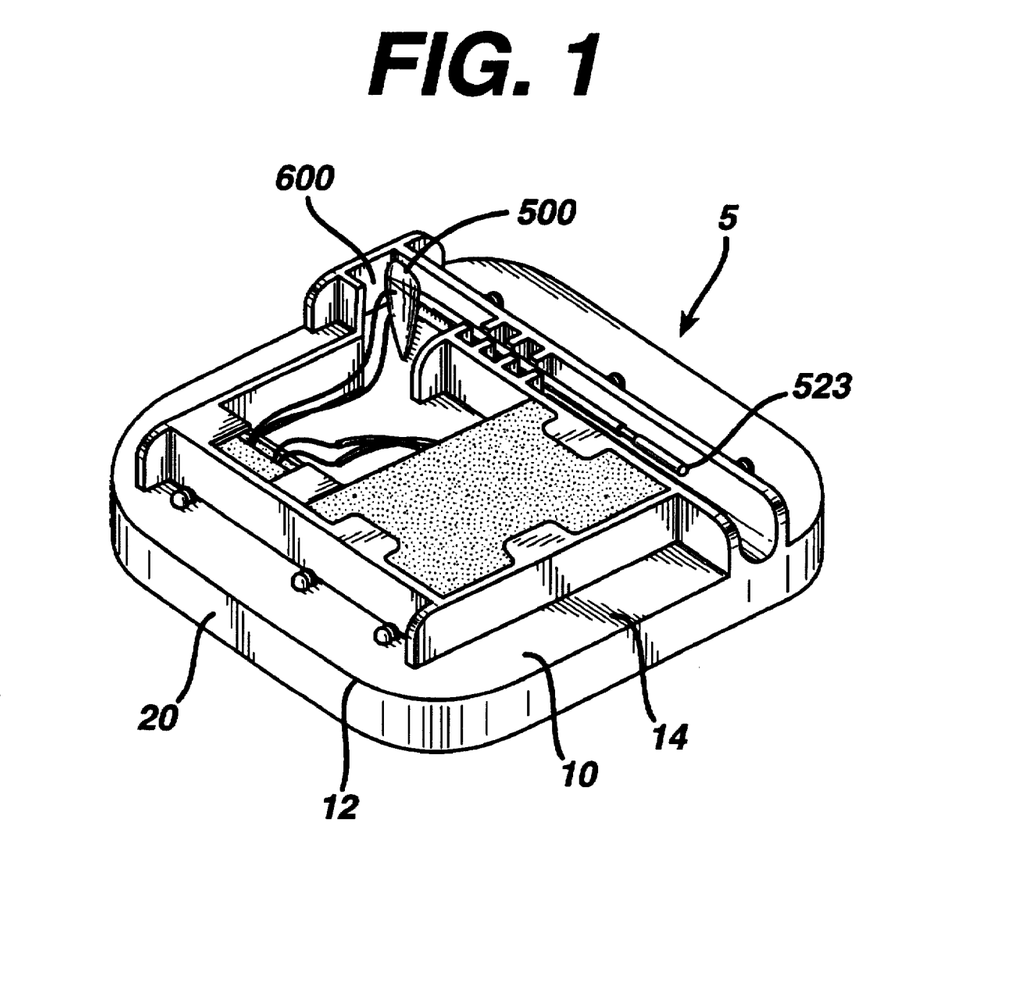
FIG. 1 is a perspective view of the package of the present invention illustrating the bottom of the package wherein the suture anchor and tip rod are seen mounted; in addition, needles are seen mounted in the foam suture park.
Figure 2:
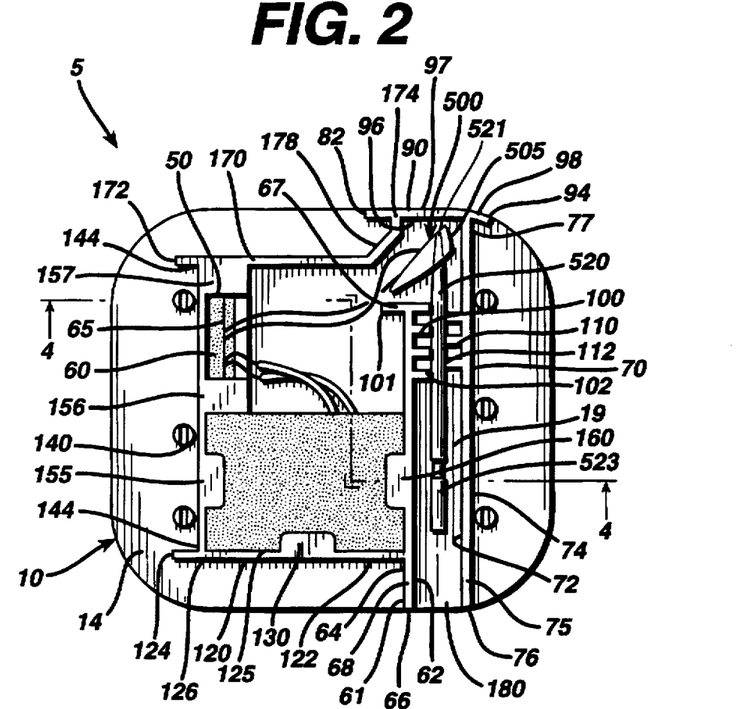
FIG. 2 is a plan view of the bottom of the package of the present invention.
Figure 10:
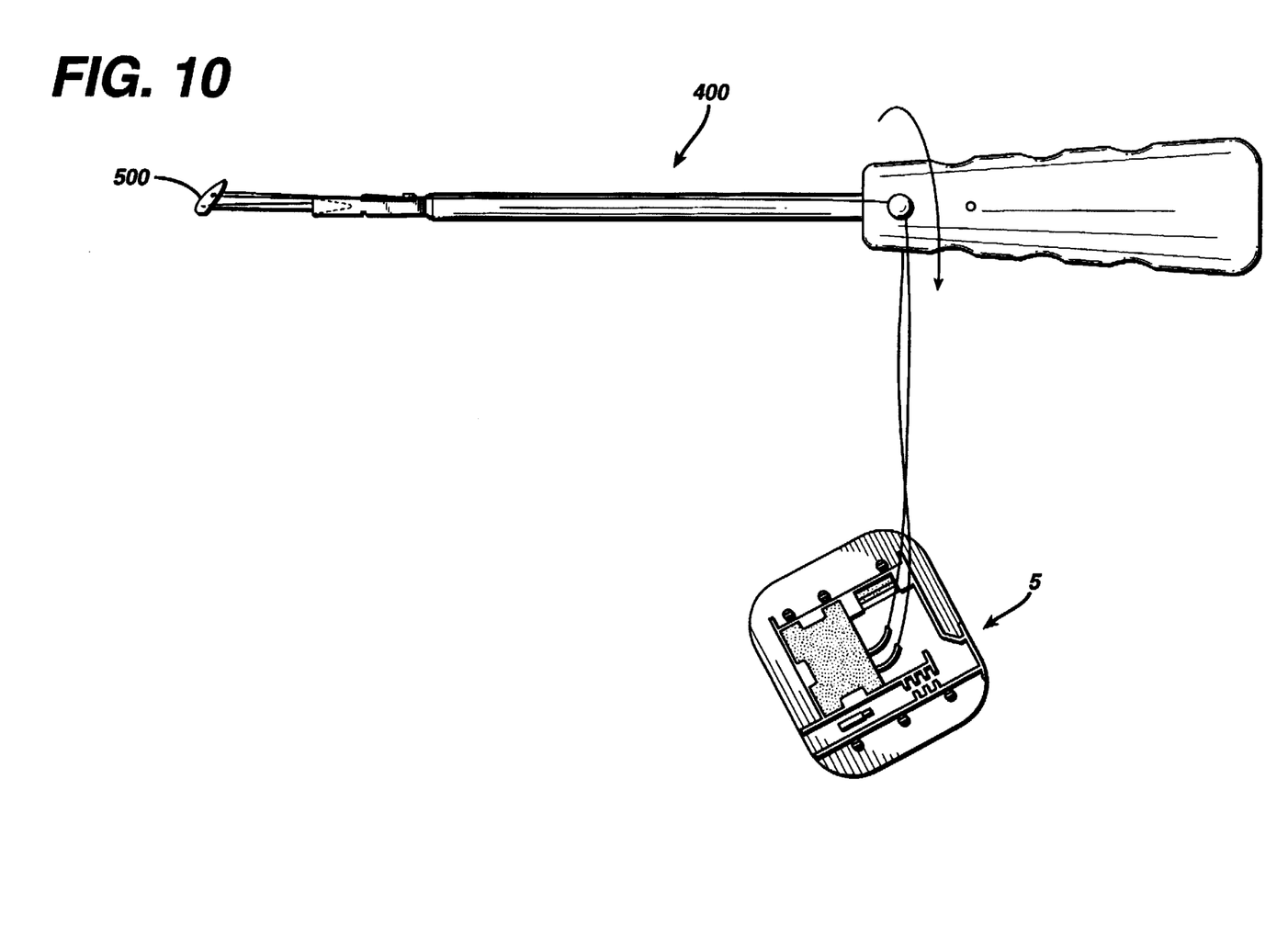
FIG. 10 is an illustration of the suture anchor and suture mounted to the applicator.

A suture anchor 500 which is especially preferred for mounting in the package 5 of the present invention is best seen in FIGS. 1, 2, and 10. Anchor member 500 is seen to be a wedge shaped member having blunt bottom end 505 and pointed top end 510. Adjacent to end 505 is a cavity 512 for receiving the distal end 521 of tip rod 520. Tip rod 520 is an elongated rod member having a circular cross-section. Rod 520 is seen to have proximal end 523. The anchor 500 is also seen to have opening 515 extending therethrough adjacent to end 510. A suture 530 is seen to be mounted in opening 515. Suture 530 has ends 535. Surgical needles 540, having pointed distal piercing tips 545 and proximal suture mounting ends 547 are mounted to the ends 535 of suture 530.

The package 5 of the present invention is seen in FIGS. 1–5. Package 5 is seen to have flat base member 10, having top side 12, bottom side 14 and outer periphery 16. Extending up from top side 12 of base member 10 about the outer periphery 16 is the outer wall 20. Outer wall 20 is seen to have top 22, outer side 24 and inner side 26. Also extending upwardly from the top 12 of base member 10, is the inner wall 30. Inner wall 30 is adjacent to outer wall 20 and is separated from outer wall 20 by a section 18 of the top side 20 of base member 10. Inner wall 30 is seen to have a top side 32, an inner side 34 and an outer side 36. Extending upward from the corners of the outer side 36 of inner wall 30 are the mounting pins 45. Pins 45 have tops 46 extending over the top of wall 30. The outer wall 20, inner wall 30, and bottom section are seen to form a winding channel 40 for a suture. Inner wall 30 is seen to have open section 38. Adjacent to the open section 38 is the suture feed opening 50 through base member 10 for passing a suture through to the bottom side 14 of base member 10. Mounted in the opening 50 is the suture friction member 60 having slit 65. Suture friction member 60 is a flat member, rectangular in shape, and preferably made from foam. The member 60 has a slit 65 which the sutures are threaded through. Slit 65 can be molded into or cut into member 60. In a preferred embodiment, member 60 is preferably substantially longer than the major dimension of hole 50 and folded back upon itself prior to mounting in hole 50 to form a slit 65. The surfaces of the opposed faces of member 60 surrounding slit 65 create a frictional drag upon the suture as it is withdrawn from the package 5.

Extending from the bottom side 14 of base member 10 are the mounting channel walls 61 and 70. Channel wall 60 is seen to have inner surface 62, outer surface 64, top 68, first end 66 and second end 67. Second mounting channel wall 70 is seen to have inner surface 72, outer surface 74, top 75 and first end 76 and second end 77. The section 19 of bottom side 14 between walls 60 and 70 is seen to form mounting channel 180. Section 19 is preferably arcuate, but may be flat. The first end 76 of wall 70 is seen to be coextensive with the outer periphery of the base member 10 while the outer end 77 is seen to intersect anchor chamber wall 90.

Anchor chamber wall 90 is seen to run along a section of the outer periphery 16 of base member 10 and to have ends 92 and 94. Chamber wall 90 has inner side 96, outer side 97 and top 98.

Extending perpendicularly from the inner side of wall 60 and the inner side of wall 70 partially into channel 180, are the rod engagement members 100, and 110 respectively. The ends 102 and 112 of members 100 and 110 are separated by gap 82. Top engagement member 100 is seen to have extension 101.

The needle park chamber bottom wall 120 is seen to extend downward from the bottom side 14 of base member 10. Wall 120 is seen to have first end 122 which intersects the outer side of all 60, and second end 124. Wall 120 is seen to have inner side 125 and outer side 126 and top 127. The rectangularly shaped needle park retention flange member 130 is seen to extend inwardly from the top 127 of the central part of the inner side 125 of wall 120. The needle park chamber side wall 140 is seen to extend downwardly from the bottom side 14 of base member 10. Side wall 140 is seen to be substantially perpendicular to wall 120 and substantially parallel to wall 60. Wall 140 is seen to have inner side 146, outer side 147, first end 142 and second end 144 and top 145. The first end 142 is seen to intersect wall 120 and the second end 144 is seen to intersect chamber top wall 160. Extending inwardly from the top 145 of the inner side 146 of wall 140 are the needle park retention flange member 155, and tab member 156 and tab member 157 on either side of opening 50. Wall member 55 is seen to connect the ends of tab members 156 and 157. Foam member 60 is retained under tab members 156 and 157. Retention flange tab member 160 is seen to extend from the top 68 of outer side 64 of wall 60. The top chamber wall 170 is seen to have first and second ends 172 and 174 and inner side 176 and outer side 177. Angulated sector 178 is seen to intersect the inner side of wall 90. The anchor chamber 200 is formed by walls 90, 70 and 100 and 170.

The anchor park foam member 210 is a generally rectangularly shaped member mounted underneath flange tab members 160, 155 and 130.

Figure 3:
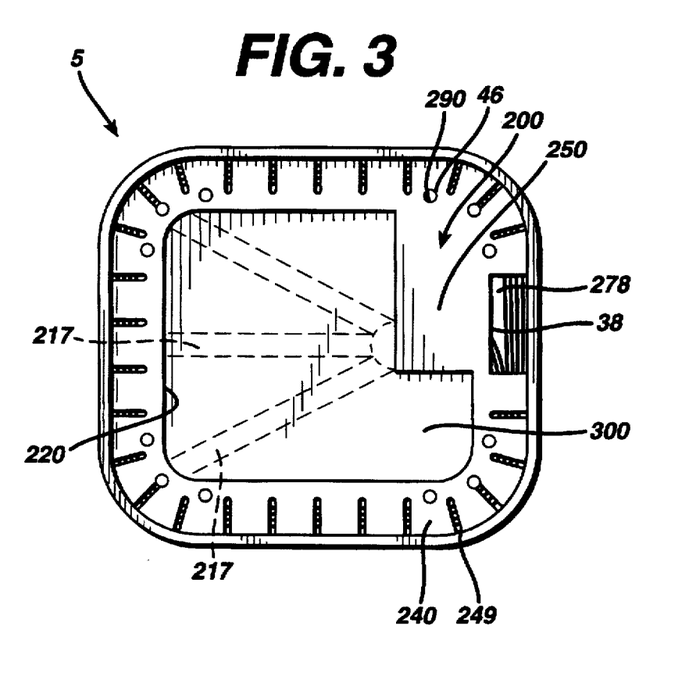
FIG. 3 is a plan view of the top of the package of the present invention.
Figure 4:
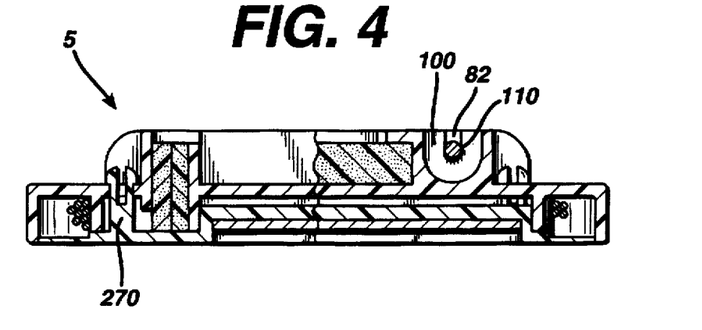
FIG. 4 is a cross-sectional view of the package of FIG. 2 taken along view line 4—4.
Figure 5:
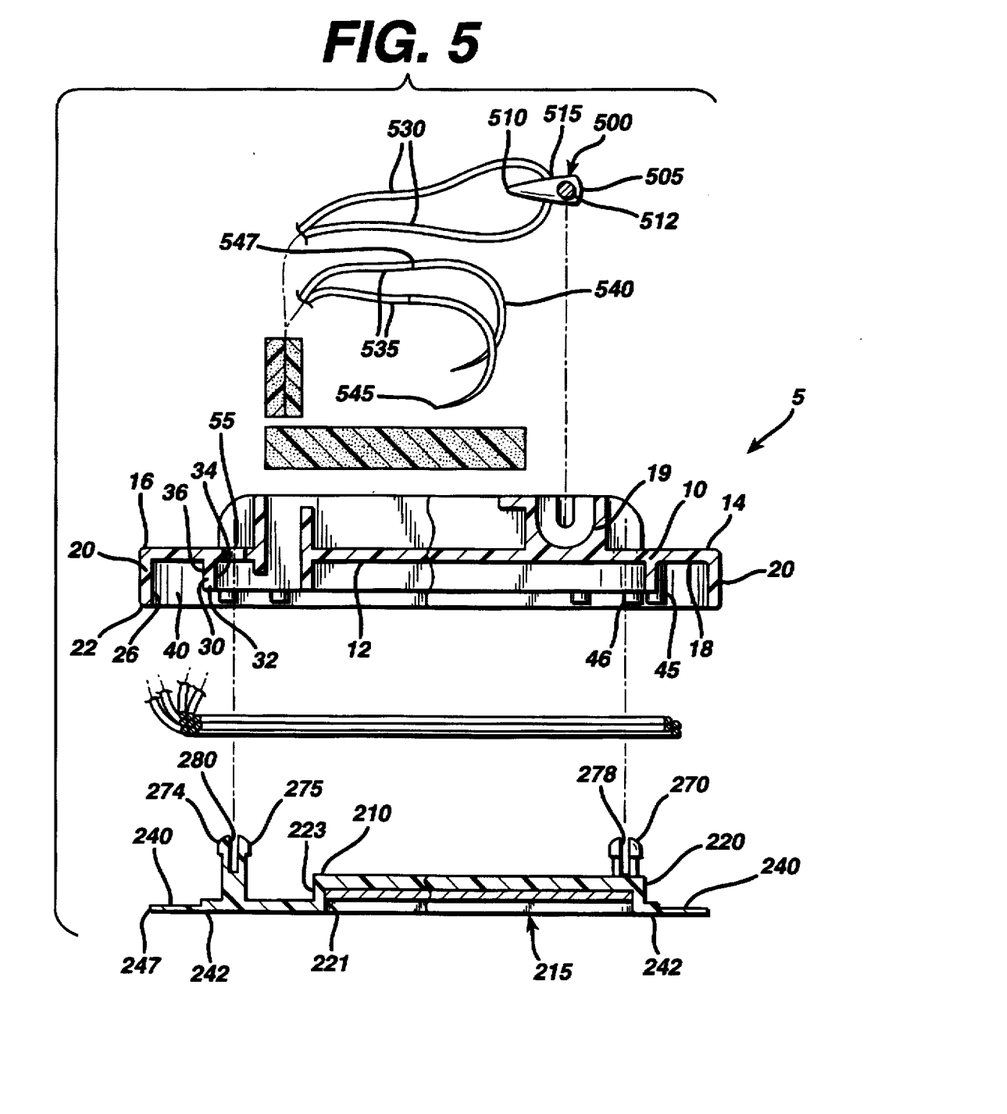
FIG. 5 is an exploded view of the cross-sectional view of FIG. 4.

The cover member 200 of the present invention is illustrated in FIGS. 3, 4, and 5. The cover member 200 is seen to have bottom member 210 having central opening 215. Structural support members 217 connect the interior of member 210 about opening 215. Extending upwardly from the top of bottom member 210 is the peripheral wall member 220. Wall member 220 is seen to have inner surface 221 and outer surface 223. Extending outwardly from the top 225 of wall member 220 are the cantilevered door members 240. Door members 240 have first end 242 affixed to the top of wall 220 and free end 247. The door members 240 essentially have a living hinge about which they pivot. The door members 240 are separated by spaces 249. Extending upwardly in one corner of the base member is the raised section 250 covering opening 50 and foam member 60. Adjacent to raised section 250 is the gap 278. Extending downwardly from the bottom of the base member 210 are the snap lock pins 270. Snap lock pins 270 are seen to have proximal ends 272 and distal ends 274 having locking flanges 275. Each snap pin 270 is separated by a gap 280 essentially dividing the locking pins in half and allowing them to be deflected inwardly toward each other. Optionally, as previously mentioned, the base member 210 may have the structural members 217 contained within space 215. Although optional, it is preferred to mount a cover member 300 on top of base member 210. The periphery 305 of cover member 300 is adjacent and pressed against the inner sides of the wall 220. Cover 200 is also seen to have pin mounting holes 290 at each corner, preferably three holes 290 although a single hole 290 may be used.

The package 5 is typically manufactured using conventional injection molding techniques. Typically, thermoplastic resins such as polyethylene and the like, which are compatible for use with sutures and medical devices, are utilized. The cover member 300 may be manufactured using conventional cutting techniques from any conventional material such as papers, plastics, and the like. It is particularly preferred to use paper for its desiccant properties.

The package 5 of the present invention is assembled as follows. Initially the needle park foam member 210- is mounted underneath the flange tab members 160, 155 and 130 on the bottom 14 of the base member 10, and foam member 360 is mounted in opening 50. Next, the suture anchor member 500 and rod tip 70 are mounted in mounting channel 180 and in the anchor chamber 600. Next, the needles 540 are mounted in the side of the needle park foam member 210. Then the suture 530 is pushed through the slit 365 in foam friction member 360 through the opening 50 in the base member 10 to the top side 12 of the base member 10. Next, the cover member 200 is mounted to the base member 10 by aligning the cover member 200 with the base member 10 and forcing the snap pins 270 through the mating openings 55 in the base member 10, while pin ends 46 from member 10 are pushed through openings 290 in member 200. Next, the suture 530 is wound into the winding channel 40 using a conventional suture winding fixture and stylus. Next, if desired, the cover member 300 is mounted on top of the bottom member 210 in opening 215. The package 5 which is now loaded with a suture anchor 500, needles 540 and suture 530, is packaged in an overwrap package which is sealed. The overwrapped package is then sterilized utilizing conventional sterilization techniques and processes. The overwrap package can be a conventional Tyvek/film package, or for packages which require a moisture-proof barrier, a conventional moisture proof foil laminate package.

Figure 6:
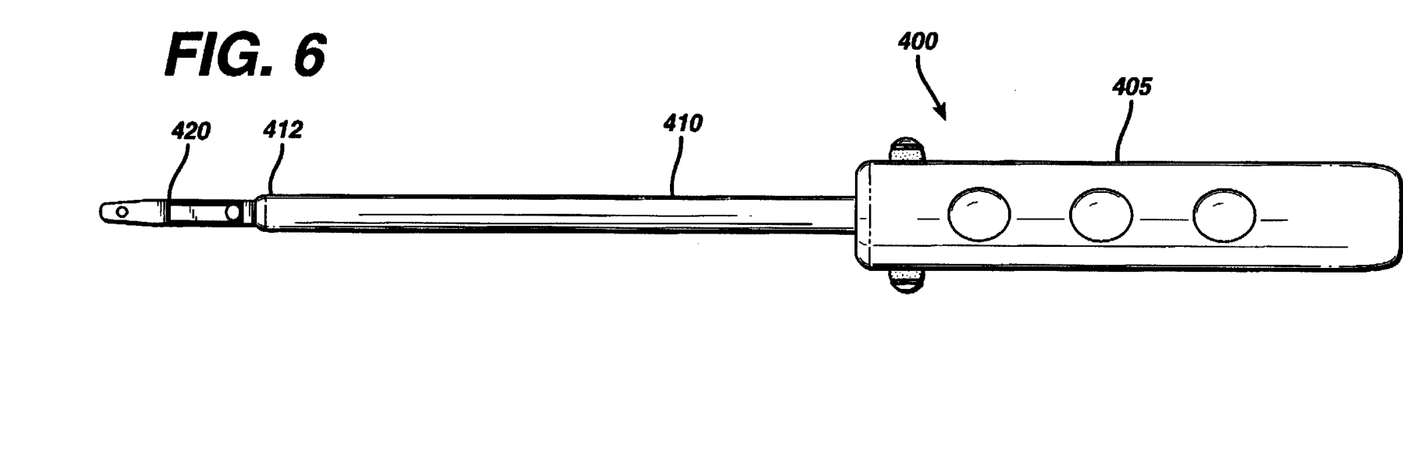
FIG. 6 is a side view of an applicator useful for applying suture anchors which may be packaged in the packages of the present invention.
Figure 7:
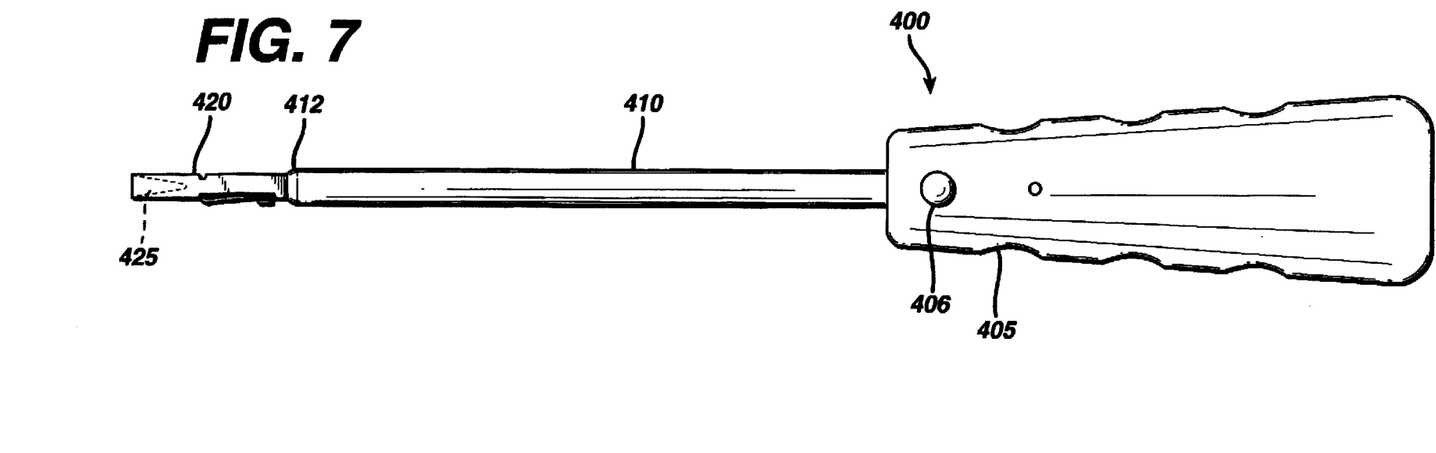
FIG. 7 is a side view of the applicator instrument of FIG. 6.

During surgery, the suture anchors 500 of the present invention are removed from the packages 5 in the following manner. First, referring to FIG. 6 and FIG. 7, a suture anchor applicator 400 instrument is illustrated. The apparatus is seen to have handle 405 distally extending rod member 410 and rod engagement member 420 mounted to the distal end 412 of rod member 410. Engagement member 420 is seen to have cavity 425 for engaging the proximal end 523 of tip rod 520.

Figure 8:
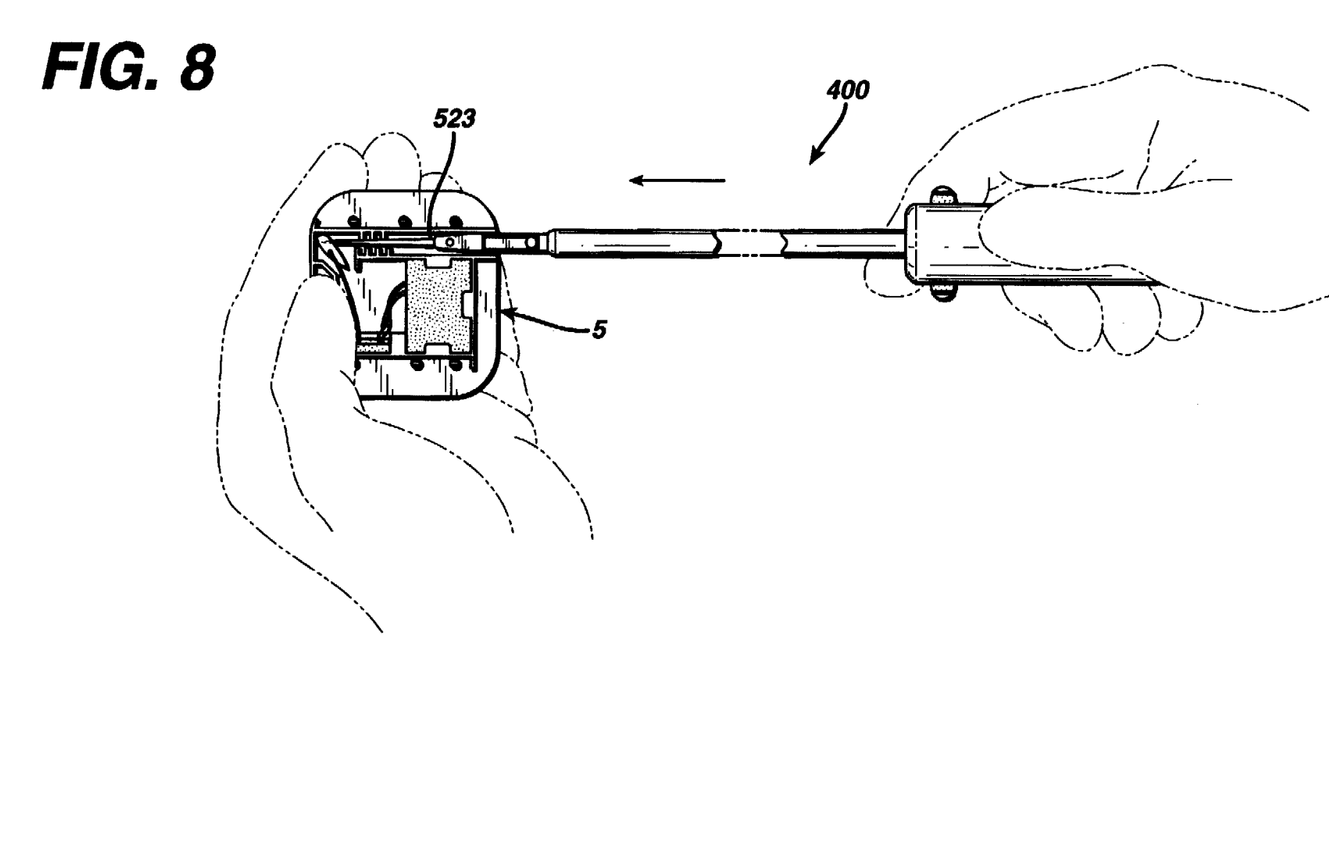
FIG. 8 is an illustration of the use of the applicator of FIGS. 6 and 7 to remove the suture anchor from the package of the present invention.
Figure 9:
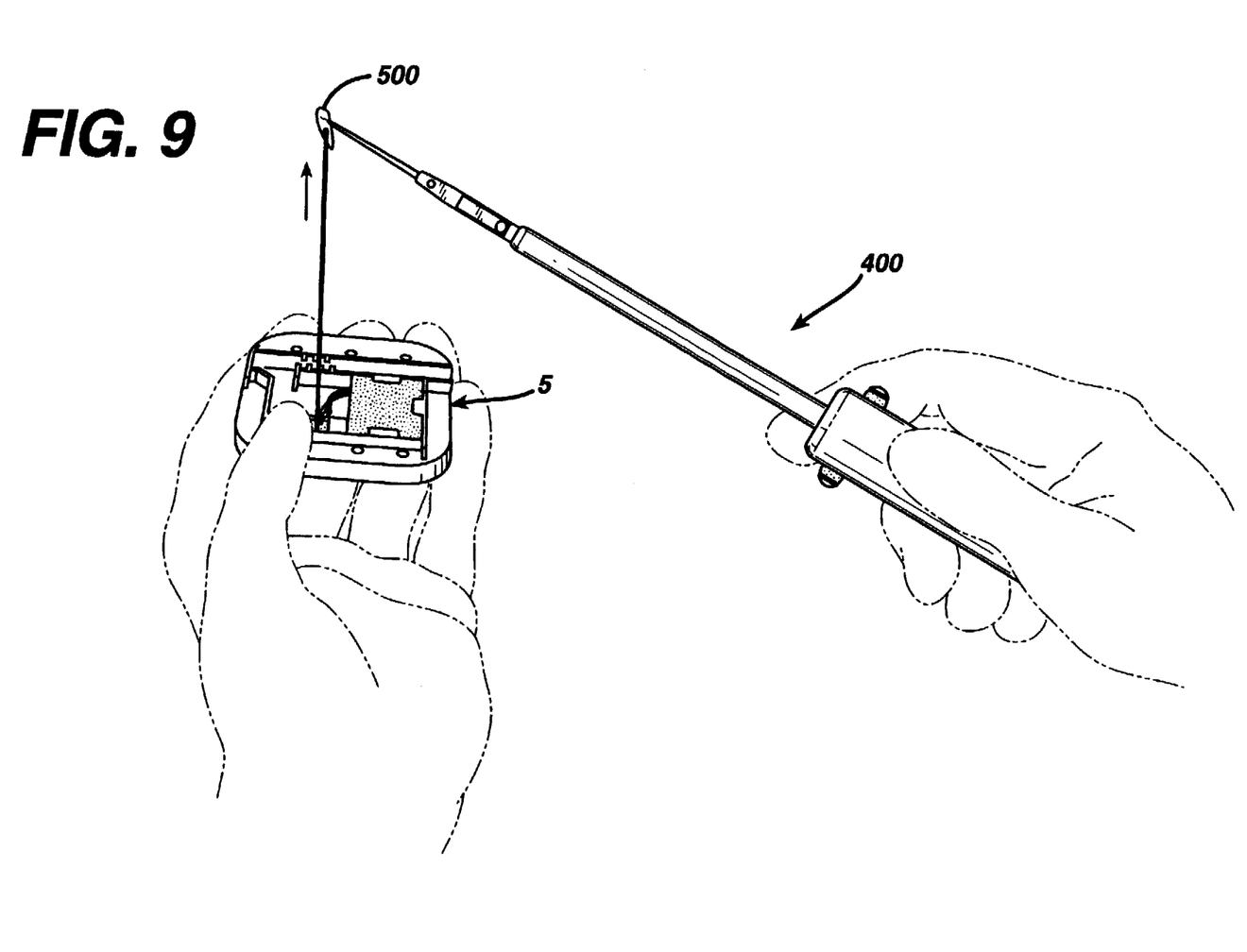
FIG. 9 illustrates the tip rod and suture anchor after having been mounted to the end of the applicator instrument and also illustrates a suture being withdrawn from the package of the present invention.
Figure 11:
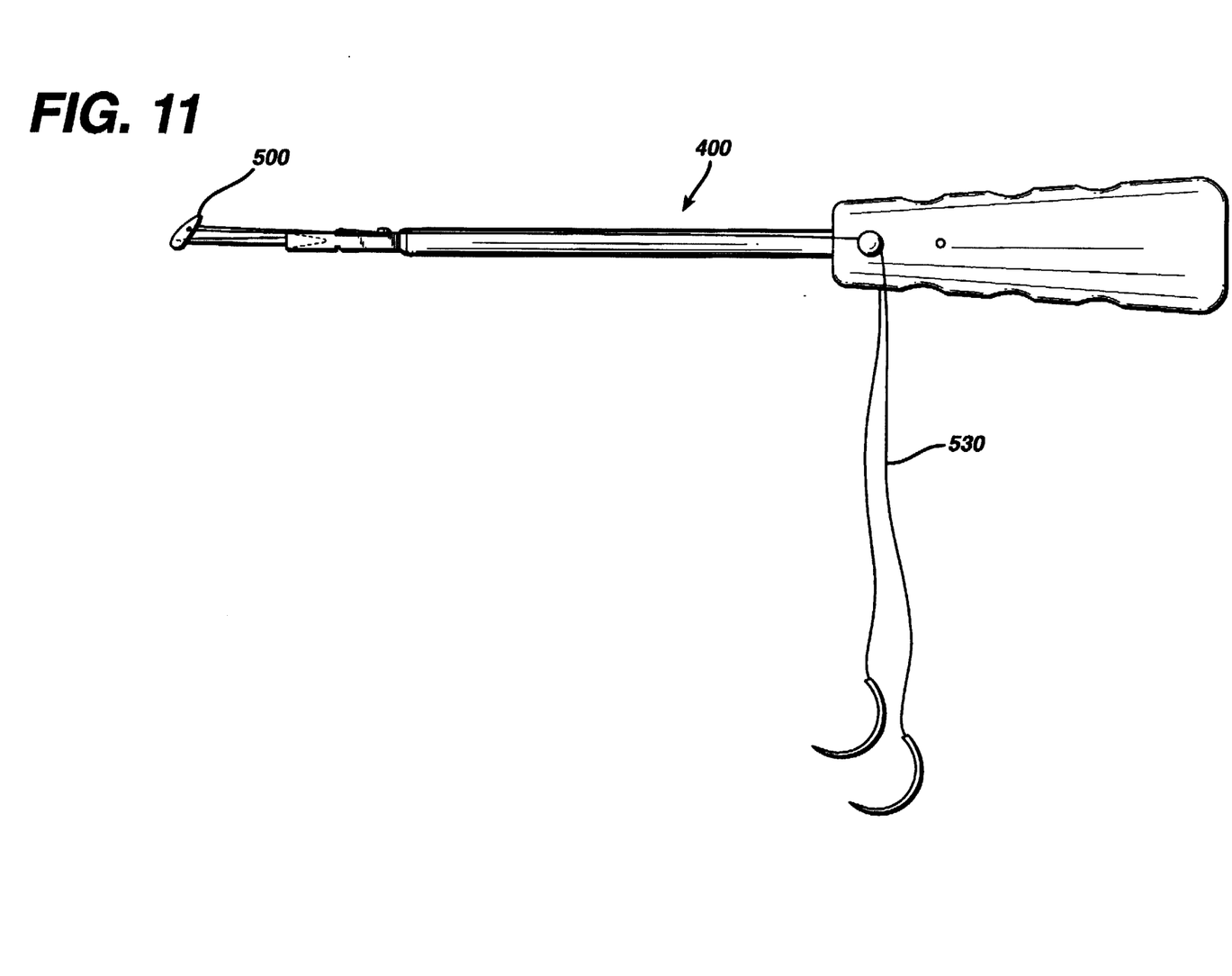
FIG. 11 illustrates the applicator having the suture anchor and suture mounted thereto with the needles removed from the suture park of the package of the present invention.
Figure 12:
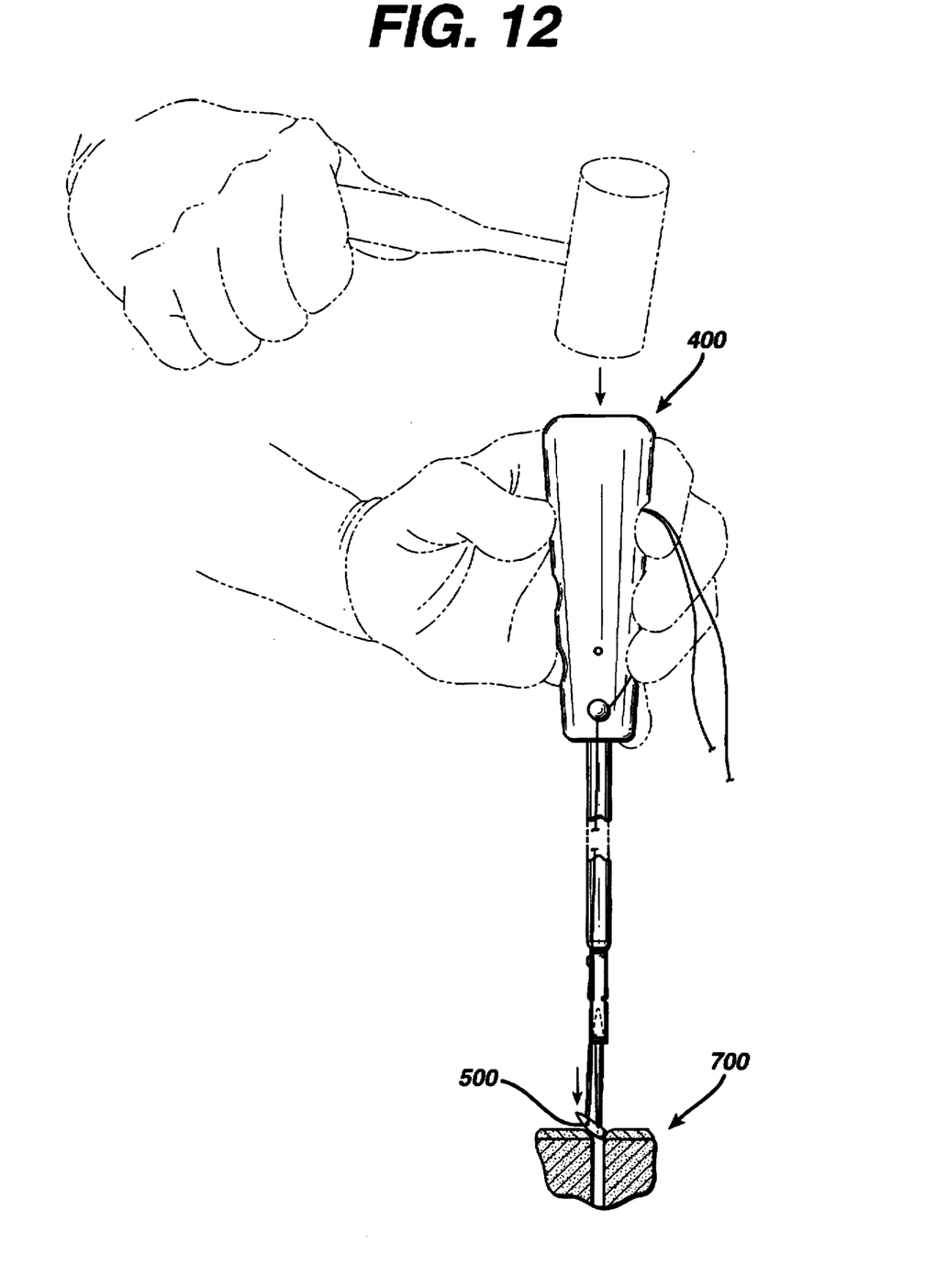
FIG. 12 illustrates a suture anchor being inserted into a bone bore hole using the applicator.
Figures 13, 14:
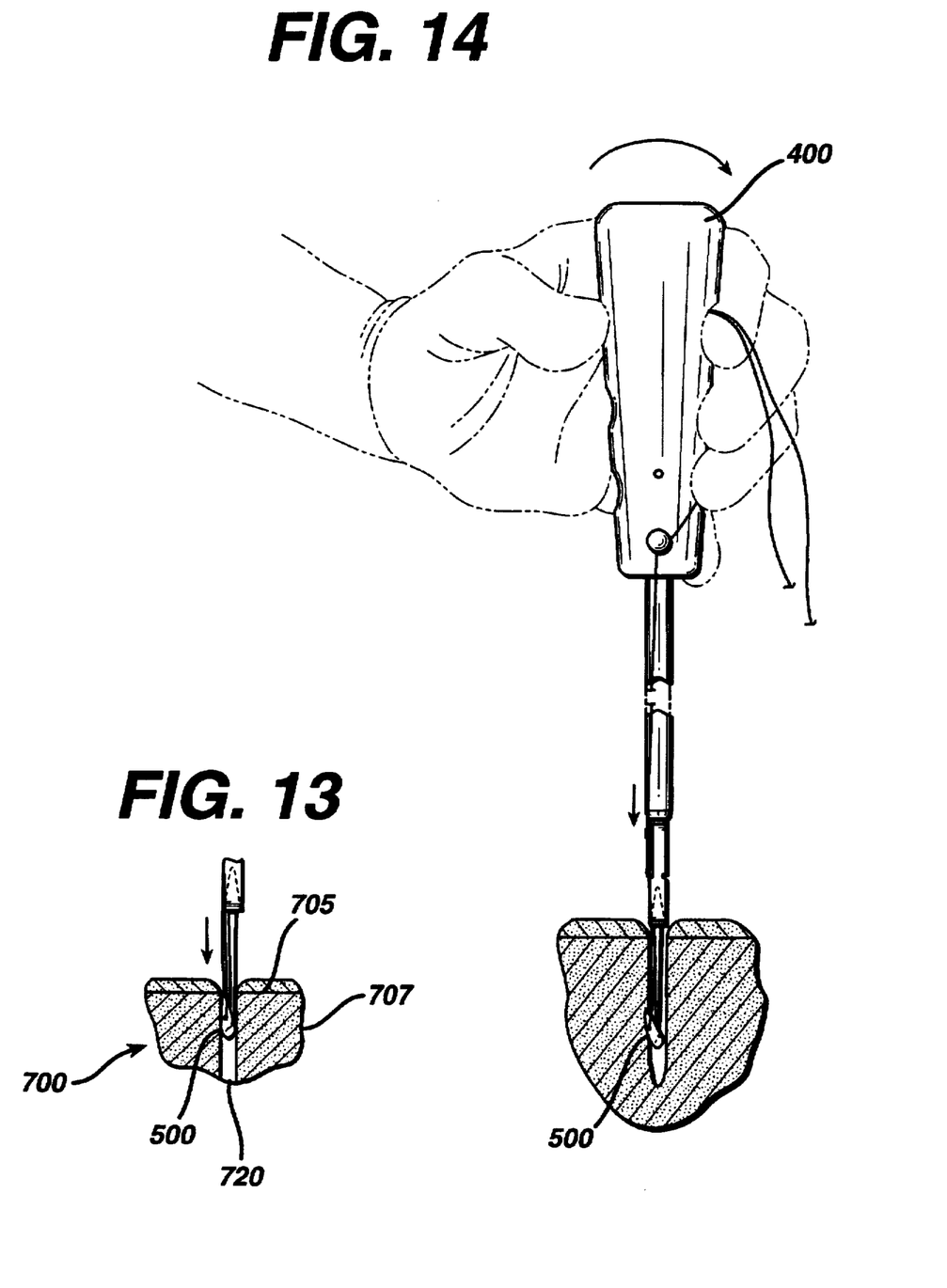
FIGS. 13–16 illustrate the emplacement and securing of the suture anchor in a bone bore hole.
Figure 15:
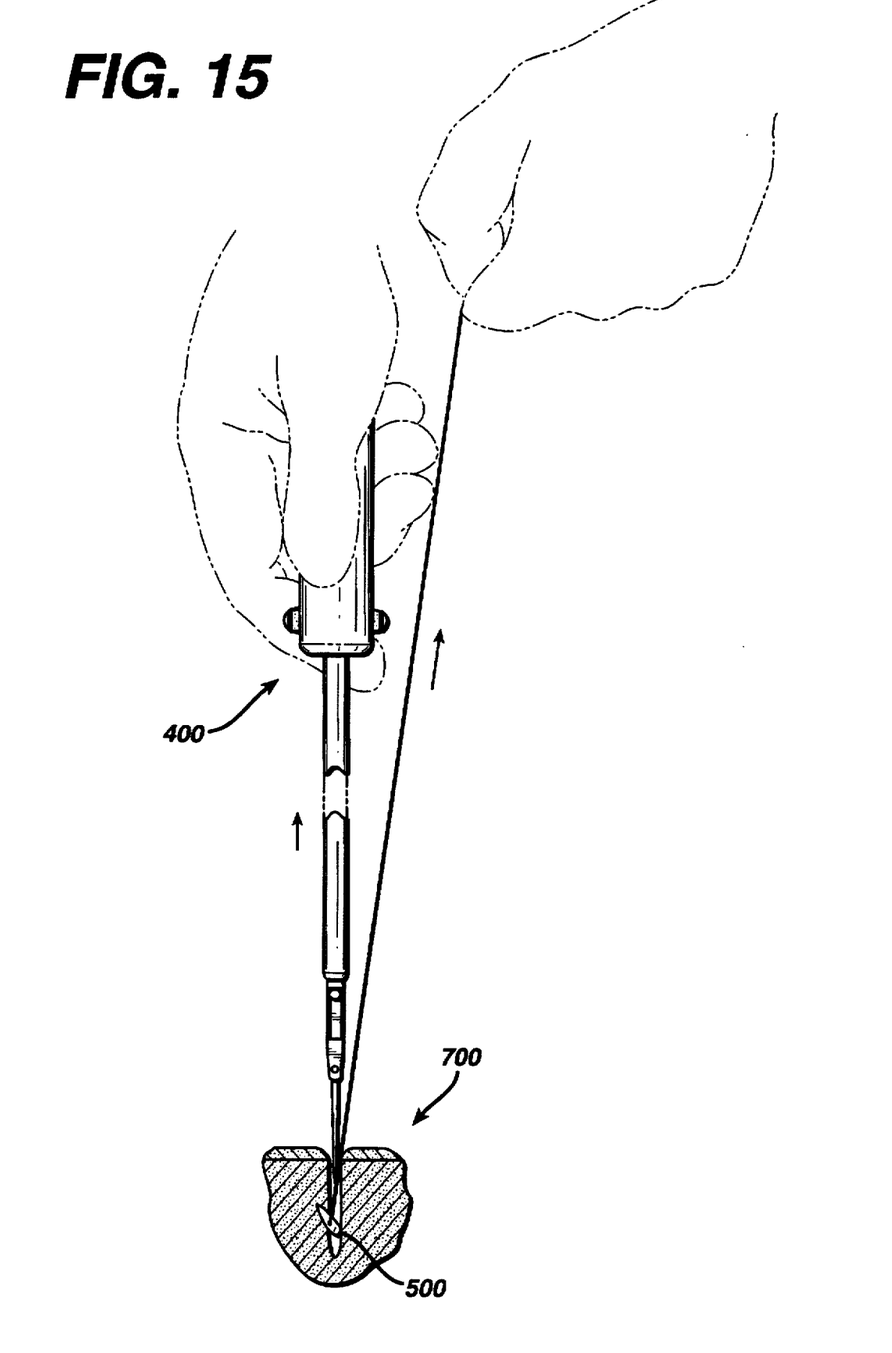
Figure 16:
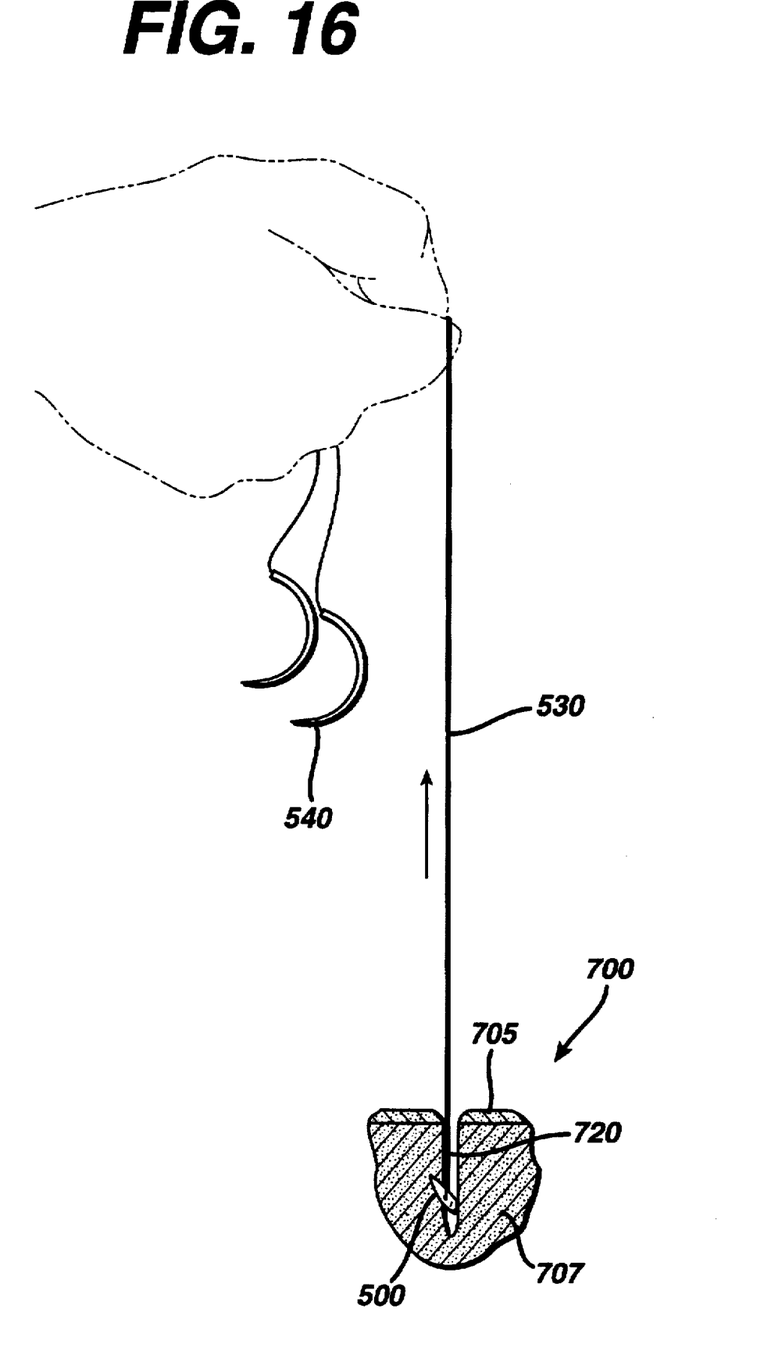

Referring now to FIG. 8, the surgeon is seen to insert engagement member into the mounting channel 80 to engage the proximal end of rod 520 in cavity 425. The rod 520 and the attached anchor member 500 are then removed from the package. As seen in FIG. 9, the surgeon then begins to withdraw the suture 530 from the package 5 through the foam friction member 360. When all of the suture 530 has been withdrawn from the winding channel 40, and the suture 530 has been engaged by the engagement pin 406 on the applicator handle 450, the surgeon then removes the needles 540 from the foam needle park 210 as seen in FIGS. 10 and 11. After drilling a bore hole 720 in bone 700 through the cortex 705 and into the underlying cancellous bone 707 the surgeon then inserts the anchor member 500 into the bone bore hole 720 as illustrated in FIGS. 12-14. Next, the surgeon tugs on both ends of the suture 530 as seen in FIG. 15 to set the anchor member 500 into the cancellous bone 707 surrounding the bore hole and then removes the applicator tip rod 520 from the anchor member 50. At this point the surgeon may use the needles 540 and sutures 530 to affix soft tissue to the surface of the bone 600.

Although this invention has been shown and described with respect to detailed embodiments thereof, it will be understood by those skilled in the art the various changes in form and detail thereof may be made without departing from the spirit and scope of the claimed invention.

We claim:

1. A package for a suture anchor, said package comprising:

a base member having a top, a bottom and an outer periphery;

an outer wall extending upwardly about the outer periphery;

an inner wall extending upwardly from the top of the base member, said wall positioned inward from the outer wall, and separated from the outer wall by a section of the top of the base member such that the inner wall, the outer wall and the section of the top of the base member form a suture winding channel;

a cover member comprising a bottom member having a central opening, and an outer periphery, an outer wall extending up from the outer periphery, said outer wall having a top, and a plurality of cantilevered door members having a fixed end and a free end extending radially out from the top of the inner wall, said door members being spaced apart;

an opening extending through the base member for receiving at least one strand of suture;

a foam member mounted on the bottom of the base member for parking needles;

first and second spaced apart parallel walls extending from the bottom of base member forming a suture anchor mounting channel, each of said first and second walls having an inner side and an outer side;

a plurality of shaft engagement walls extending perpendicularly from the inner sides of the first and second parallel walls, said walls extending partially into the suture anchor mounting channel;

means extending from the bottom of the cover member for mounting to the base member;

means in the base member for receiving the mounting means of the cover member;

means extending from the inner wall of the base member for mounting the cover member; and means in the cover member for receiving the mounting means of the base member, wherein the cover member is mounted to the base member such that the cantilevered members extend over the suture channel.

2. The package of claim 1 wherein the cover member mounting means comprises at least two locking pins extending form the bottom of the cover member, said pins having a longitudinal slit, and distal locking rims extending radially outward from the ends of the pins.

3. The package of claim 1 wherein the base member receiving means comprises at least two holes for receiving and engaging the cover locking pins.

4. The package of claim 1 further comprising a paper cover mounted over the opening.

5. The package of claim 1 wherein the base member mounting means comprises at least one pin having an end extending from the inner wall.

6. The package of claim 1 wherein the cover receiving means comprises at least one hole.

* * * * *